(12) United States Patent
Baro et al.

(10) Patent No.: US 8,772,532 B2
(45) Date of Patent: Jul. 8, 2014

(54) PROCESS FOR PREPARING (METH)ACRYLIC ESTERS OF POLYOLS

(75) Inventors: Juergen Baro, Esslingen (DE); Jean-Marc Ballin, Noisy le Grand (FR)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/564,956

(22) Filed: Aug. 2, 2012

(65) Prior Publication Data

US 2013/0035504 A1 Feb. 7, 2013

Related U.S. Application Data

(60) Provisional application No. 61/514,510, filed on Aug. 3, 2011.

(51) Int. Cl.
C07C 67/03 (2006.01)
C07C 69/52 (2006.01)

(52) U.S. Cl.
USPC .......................................... 560/204; 560/205

(58) Field of Classification Search
USPC .................................................. 560/204, 205
See application file for complete search history.

(56) References Cited

U.S. PATENT DOCUMENTS

| | | | |
|---|---|---|---|
| 4,187,383 A | 2/1980 | Cowherd et al. | |
| 5,159,106 A * | 10/1992 | Ritter et al. | 560/224 |
| 5,976,324 A * | 11/1999 | Groschl et al. | 203/14 |
| 6,838,515 B2 | 1/2005 | Derks et al. | |
| 6,903,231 B1 | 6/2005 | Fies et al. | |

FOREIGN PATENT DOCUMENTS

| | | | |
|---|---|---|---|
| EP | 0127766 | | 12/1984 |
| EP | 0449919 | | 5/1994 |
| EP | 0890568 | * | 1/1999 |
| EP | 0890568 | | 8/2001 |
| EP | 1204472 | | 1/2003 |
| GB | 1489536 | | 10/1977 |

OTHER PUBLICATIONS

Hall, R. H. et al., "'Just How Pure Are Your Monomers?' A Chemical Analysis of Some Common Reactive Diluents", 1987, pp. 56-64.
Marek, Thomas et al., "Characterization of Acrylates Used for UV-Curable Resins by GC/MS", *DIC Technical Review*, No. 5 1999, pp. 85-93.
Matsunaga, Morikatsu et al., "Characterization of Oligomeric Polypropyleneglycol Acrylate by GC, SFC, and Maldi-Tof-MS", *Analytical Sciences*, vol. 18 2002, pp. 277-281.
Matsunaga, Morikatsu et al., "Optimization of Conditions for Detailed Compositional Analysis of Acrylic Oligomers by Supercritical Fluid Chromatography with Temperature Programming or Modifier Gradient Technique", *Analytical Sciences*, vol. 17 2001, pp. 1295-1299.
Shiau, Lie-Ding et al., "Consecutive Esterification of 1,4-Butanediol with Acrylic Acid by Homogeneous Catalysis", 2000, pp. 133-148.
Yoo, Seong J. et al., "Mass Spectrometry and Gas Chromatographic Retention Indices of Selected UV/EB-Curable Monomers and Photoinitiators Commonly Used in Food Packaging Print and Coating Formulations", *Radtech Report* 2004, pp. 60-68.

* cited by examiner

*Primary Examiner* — Fereydoun G Sajjadi
*Assistant Examiner* — Mark Luderer
(74) *Attorney, Agent, or Firm* — Servilla Whitney LLC

(57) ABSTRACT

Provided are processes for the production of (meth)acrylic esters of polyols, in which for 80 mol % or more of the esters, all of the OH groups of the polyols are esterified. Certain processes relate to reaction of polyols with acrylic acid and/or methacrylic acid in the presence of acidic esterification catalysts and in the presence of polymerization inhibitors, operating with reaction mixtures which are liquid at reaction temperature and are free from nonreacting solvents and/or azeotropic entrainers, the resultant water of condensation being stripped from the gas phase of the reaction space, and the (meth)acrylic acid is metered in three or more portions.

10 Claims, 4 Drawing Sheets

PROCESS FOR PREPARING (METH)ACRYLIC ESTERS OF POLYOLS

CROSS REFERENCES TO RELATED APPLICATIONS

This application claims priority to U.S. Provisional Application 61/514,510, filed Aug. 3, 2011, the contents of which are incorporated by reference.

FIELD

Aspects of the invention generally relate to processes for preparing (meth)acrylic esters of polyhydric alcohols (polyols).

BACKGROUND (Meth)acrylic esters of polyhydric alcohols, more particularly from the group of the dihydric to hexahydric aliphatic saturated alcohols, and their oxalkylation products, are finding increasing importance as high-reactivity ingredients in radiation-curing systems. Such polyfunctional (meth)acrylic esters can be used, for example, as coatings raw materials for electron beam curing or as an ingredient of UV-curing printing inks or corresponding coating materials, filling compositions, molding compositions or casting compositions, and also in adhesives, more particularly those which cure anaerobically. Their preparation, however, is not without problems. The requirement in particular is for colorless products with a low acid number and high storage stability, which also have virtually no inherent odor. Distillative purification of the (meth)acrylic esters of the type in question here is generally ruled out by their high molecular weight and their high reactivity. The products are therefore to be obtained directly, as very largely colorless reaction products, from the esterification Implementing the esterification reaction requires the accompanying use of high-activity inhibitors, which in turn do not trigger any unwanted secondary reactions, such as discolorations, for example.

The predominant industrial production process for the direct esterification of (meth)acrylic acid with hydroxy compounds is based on the use of volatile organic solvents as a liquid reaction medium, also known as solvent operation. Suitable volatile organic solvents are, for example, toluene, cyclohexane, methylcyclohexane or n-heptane, which, moreover, are utilized as an azeotropic entrainer for the continuous removal of the resultant water of reaction from the reaction mixture and are removed by distillation after the end of reaction. Corresponding process descriptions are found in U.S. Pat. No. 6,838,515 and EP-A-127,766, for example. In spite of the distillative removal of the volatile organic solvents after the end of reaction, however, monomer and oligomer (meth)acrylates prepared in this way always have residual solvent traces, the amounts of which vary in the range of 50-10 000 ppm.

Since the use of organic solvents is being regulated to increasing degrees due to environmental protection considerations, there is an increasing need for an alternative production process, in which the direct esterification of (meth) acrylic acid with hydroxy compounds may be carried out in (meth)acrylic acid itself as the liquid reaction medium, without use of volatile organic solvents (also known as solvent-free operation). The water of reaction formed is removed from the reaction mixture by distillation, in the form of a water/(meth)acrylic acid mixture. Corresponding processes are described in EP-B-449 919 and EP-B-1 204 472, for example. In this way, completely solvent-free monomer and oligomer (meth)acrylates can be prepared, and are used in applications including those where traces of volatile organic solvents may produce an unwanted inherent odor, such as in the packaging sector, for example.

Both production technologies have been subject to continuous ongoing development over the course of the years, with the focal points being on optimizing the throughput and minimizing the use of raw materials. The resulting purity of the monomer and oligomer (meth)acrylates prepared in this way, in contrast, has been paid no great attention to date. The purity, in the relevant technical literature, is generally understood to be the total amount of fully and partially (meth) acrylated species of substance in the end product, and is calculated from the residual amount of unreacted hydroxy compounds and situated, accordingly, at usually more than 97% (GC area-percent).

Strictly speaking, however, this widespread definition of the concept of purity says nothing about the amount that is actually present of the desired, fully (meth)acrylated species of substance in the end product, and is therefore unsatisfactory. In the context of the present invention, therefore, "purity" means the amount of fully (meth)acrylated species of substance in (meth)acrylic esters. Fully (meth)acrylated species of substance are understood to be those in which all of the OH groups of the alcohol component of the (meth)acrylic ester are present in esterified form.

This definition of the term purity, which applies strictly in the context of the present invention, is particularly important in view in particular of the fact that, for polyfunctional monomer and oligomer (meth)acrylates, the identification and classification of substances under REACH (Registration, Evaluation, Authorization and Restriction of Chemicals) is exclusively via CAS numbers, with corresponding purity requirements related to the respective fully (meth)acrylated species of substance (see ECHA publication "Guidance for Identification and Naming of Substances under REACH—June 2007"). For instance, for what REACH calls "mono-constituent substances", which include, for example, 1,6-hexanediol diacrylate, tripropylene glycol diacrylate and trimethylolpropane triacrylate, for example, purities of at least 80%—based on the desired, fully acrylated species of substance—in the end product are required.

From the technical literature it is known that, for example, polyfunctional monomer acrylates such as 1,6-hexanediol diacrylate, tripropylene glycol diacrylate, trimethylolpropane triacrylate and pentaerythritol tetraacrylate constitute mixtures of species of substance having different degrees of acrylation with other by-products, in which the desired, fully acrylated species of substance is only part of the mixture (cf. R. H. Hall, F. P. B. Van Der Maeden, A. C. C. M. Willemsen, Spec. Chem., 7, 56-64 (1987) and M. Matsunaga, Y. Matsushima, H. Ohtani, S. Tsuge, Anal. Sci., 17, 1295-1299 (2001)).

Even more complex compositions are a characteristic of those polyfunctional monomer and oligomer (meth)acrylates that are based on polyhydroxy compounds alkoxylated with ethylene oxide and/or propylene oxide. As an inevitable concomitant of the process, such products always have a distribution curve with different degrees of alkoxylation around a middle value, and so the number of possible species of substance (meth)acrylated fully and partially is not only dependent on the number of available hydroxyl groups but is also connected, on a multiplicative basis, with the number of differently alkoxylated polyhydroxy species.

Corresponding investigations into the composition of such polyfunctional, alkoxylated monomer and oligomer acrylates, such as ethoxylated 1,6-hexanediol diacrylate, propoxylated neopentylglycol diacrylate, ethoxylated trimethylolpropane triacrylate, propoxylated glycerol triacrylate and polypropylene glycol diacrylate, are found in T. Marek, U. Gröllman, DIC Technical Review, No. 5, 85-93 (1999), M. Matsunaga, Y. Matsushima, H. Yokoi, H. Ohtani, S. Tsuge, Anal. Sci., 18, 277-281 (2002) and S. J. Yoo, G. V. Pace, B. K. Khoo, J. Lech, T. G. Hartman, RadTech Report, May/June, 60-68 (2004).

The acidically catalyzed, direct esterification of (meth) acrylic acid with monohydroxy compounds can be considered in a first approximation still to be a simple phase equilibrium reaction, in which the phase equilibrium can be shifted almost entirely to the product side by the continuous removal of the water of reaction from the reaction mixture, via the appropriate choice of temperature, pressure and reaction time.

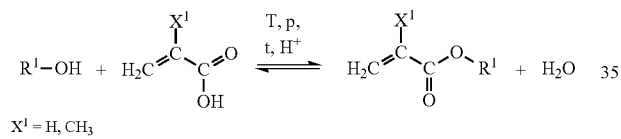

The end product generally contains the desired, fully (meth)acrylated species of substance in purities of greater than 97%.

For polyhydroxy compounds, in contrast, the profile of the acidically catalyzed, direct esterification of (meth)acrylic acid is substantially more complex, as described in L. -D. Shiau, T. -R. Ling, D. -S. Tseng, Chem. Eng. Comm , 179, 133-148 (2000), since different phase equilibrium reactions, coupled with one another, take place alongside one another, and may also result, depending on reaction regime, in substantial amounts of partially (meth)acrylated monomer or oligomer (meth)acrylates in the end product.

Furthermore, as set out by R. H. Hall, F. P. B. Van Der Maeden, A. C. C. M. Willemsen, Spec. Chem., 7, 56-64 (1987), these partially (meth)acrylated monomer or oligomer (meth)acrylates—and also unreacted (meth)acrylic acid and unreacted polyhydroxy compounds—may enter into secondary reactions such as Michael additions with the fully (meth) acrylated species of substance, and also with one another.

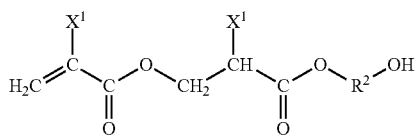

Michael Adduct Mono(meth)acrylate/(meth)acrylic Acid

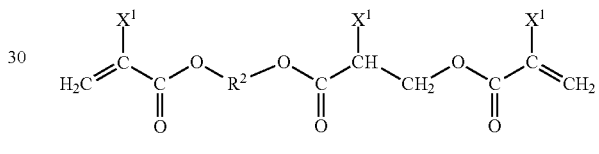

Michael Adduct Di(meth)acrylate/(meth)acrylic Acid

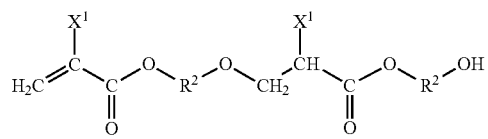

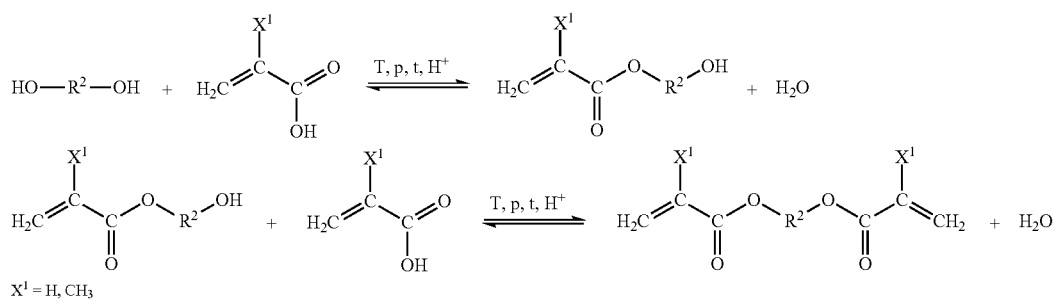

Michael Adduct
Mono(meth)acrylate/mono(meth)acrylate

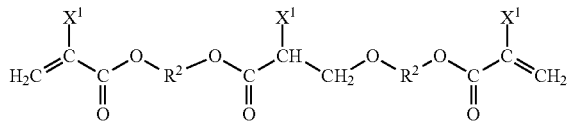

X¹ = H, CH₃

Michael Adduct
Di(meth)acrylate/mono(meth)acrylate

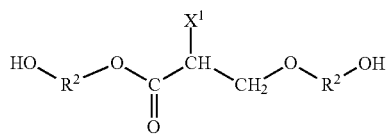

X¹ = H, CH₃

Michael Adduct Mono(meth)acrylate/diol

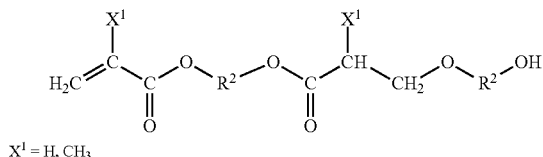

X¹ = H, CH₃

Michael Adduct Di(meth)acrylate/diol

The presence of partially (meth)acrylated monomer or oligomer (meth)acrylates and of Michael adducts in the end product leads inevitably to a considerable loss of purity relative to the desired, fully (meth)acrylated species of substance.

Although many known monomer acrylates such as 1,6-hexanediol diacrylate, tripropylene glycol diacrylate, trimethylolpropane triacrylate or pentaerythritol tetraacrylate contain more than 97% of acrylated species of substance, the amount therein of the desired, fully acrylated species of substance is nevertheless often significantly below 80%. The unwanted by-products such as Michael adducts or partially acrylated species of substance in these products do not only cause a reduced purity, but may also considerably influence the profile of properties. For instance, partially (meth)acrylated monomer and oligomer (meth)acrylates lead to higher viscosities because of the formation of hydrogen bonds via their free hydroxyl groups, and also to detractions from the reactivity, owing to an absence of double bonds. Michael adducts, on account of their high molecular weight, likewise produce an increase in viscosity and lower the density of double bonds, since double bonds are consumed when the adducts are formed.

DETAILED DESCRIPTION

Figure 1:
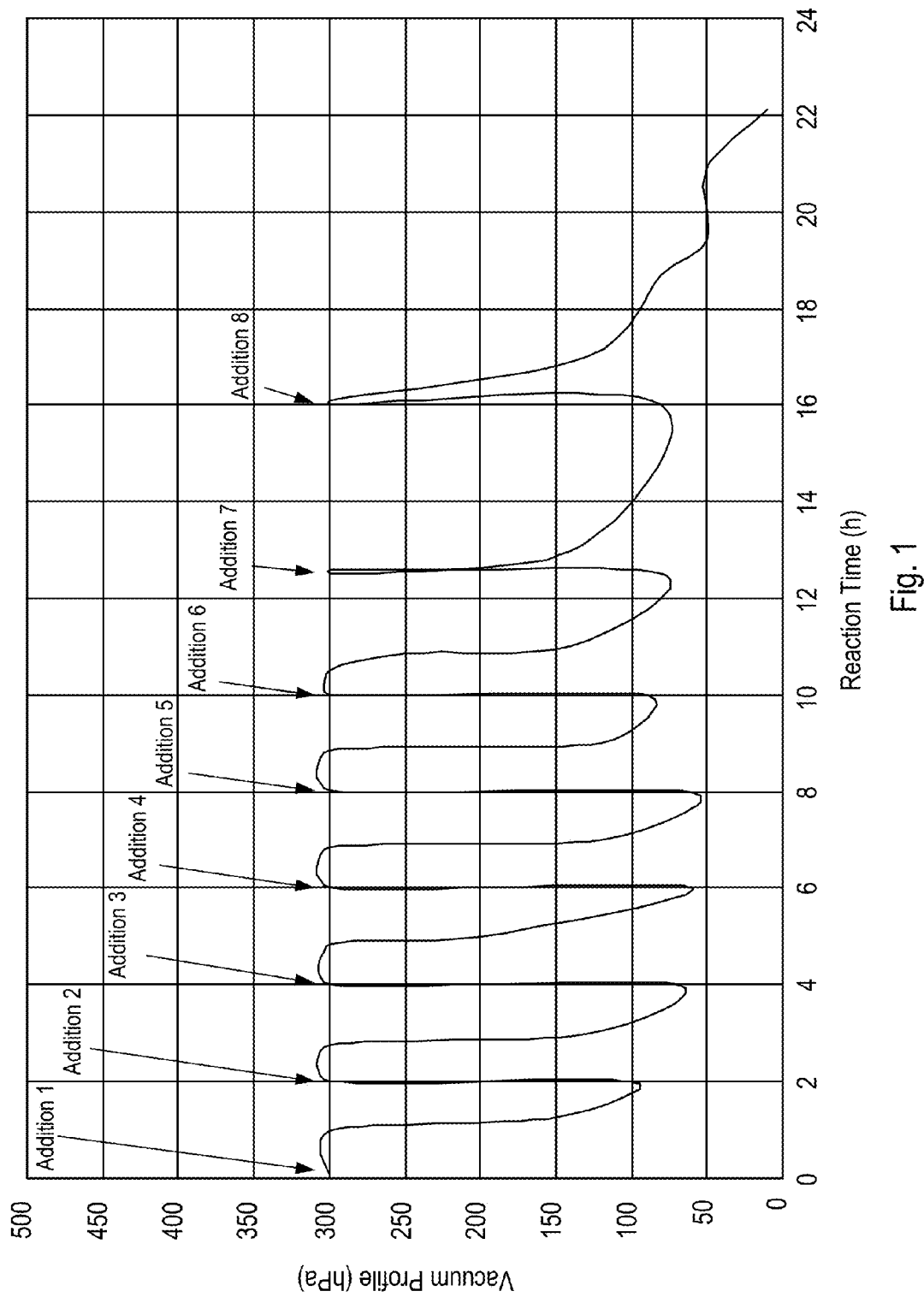
FIG. 1 is a graph showing the vacuum profile versus a reaction time during a process stage of a reaction in accordance with one or more embodiments of the present invention.

One aspect of the invention relates to new processes for preparing solvent-free (meth)acrylic esters of polyhydric alcohols. In one or more embodiments of the the (meth) acrylic esters made from processes described herein, at least 80 mol % of the OH groups present in the polyols used are in esterified form, corresponding to a purity of at least 80% in the sense of the definition set out above.

Surprisingly, it has been found that the addition of (meth) acrylic acid in portions to polyols, with subsequent or simultaneous removal of the water of reaction formed in the esterification, results in a purity of at least 80%, relative to the desired, fully acrylated species of substance in the end product, it being necessary for specific parameters to be observed.

The present invention provides a process for preparing (meth)acrylic esters of polyols, the amount in these esters of species in which all of the OH groups of the polyols are esterified being 80 mol % or more, by reaction of polyols with acrylic acid and/or methacrylic acid in the presence of acidic esterification catalysts and in the presence of polymerization inhibitors, operating with reaction mixtures which are liquid at reaction temperature and are free from nonreacting solvents and/or azeotropic entrainers, the resultant water of condensation being stripped from the gas phase of the reaction space, characterized in that (meth)acrylic acid is metered in three or more portions, with the following provisos:
the amount of the individual (meth)acrylic acid portions is set in each case in the range from 5 to 40 mol %, based on the entirety of the OH groups of the polyols used,
the number of (meth)acrylic acid portions, multiplied by the amount of (meth)acrylic acid portions used (in mol %), produces a figure of at least 100 (mol %),
the reaction temperature is set to a level in the range from about 70 to about 150° C., and
the water formed in the reaction is removed from the reaction space under reduced pressure, the reduced pressure being about 600 hPa or less.

By "nonreacting solvents and/or azeotropic entrainers" are meant those solvents and azeotropic entrainers, respectively, which are chemically inert under the reaction conditions of the process of the invention. The above phrase "operating with reaction mixtures which are liquid at reaction temperature and which are free from nonreacting solvents and/or azeotropic entrainers" means, therefore, that such solvents or azeotropic entrainers are not used in the process of the invention.

As stated, the metering of (meth)acrylic acid takes place in three or more portions. In this context it is also possible to refer to successive process stages. The first metered addition of (meth)acrylic acid is in this sense the first process stage, the second metered addition of (meth)acrylic acid then being the second process stage, and so on.

In one or more embodiments, after addition of each (meth) acrylic acid portion, a vacuum gradient is applied such that the reaction mixture boils continuously.

In some embodiments, the water formed during the reaction is removed continuously from the reaction space.

In one or more embodiment, each subsequent (meth) acrylic acid portion is metered in only when the acid number of the reaction mixture has dropped below a level of about 100 mg KOH/g. In further embodiments, the acid number of the reaction mixture in the subsequent process stage is equal to or higher than that in the preceding process stage. In one or more embodiments, in the last process stage, the acid number is set lower than the acid number of the penultimate process stage.

This has the advantage that it shortens the downstream alkaline washing stages, particularly since the acid number in the final end product is adjusted preferably to a level of below 1 mg KOH/g, so that the end product is stable in storage and so that autocatalytic acidic hydrolysis of the acrylate and an associated loss in product properties are avoided.

In one or more embodiments, the (meth)acrylic acid is metered in 4 to 16 portions.

In further embodiments, the (meth)acrylic acid is metered in an equal amount in each case, and in further embodiments, in amounts in each case in the range from about 5 to 25 mol %, and in even further embodiments, in the range from about 10 to 20 mol %.

In one or more embodiments, the total amount of the (meth)acrylic acid portions metered in is 105 to 160 mol %, based on the entirety of the OH groups of the polyols used.

"Polyols," in the context of the present specification, are organic substances having two or more OH groups per molecule. The individual OH groups of the polyols may, in each case independently of one another, be primary, secondary or tertiary OH groups. Examples of suitable polyols include aliphatic, cycloaliphatic or aromatic polyhydroxy compounds. Examples of suitable polyols include, for instance, the following: glycerol, trimethylolpropane, tripropylene glycol, dipropylene glycol, 1,4-cyclohexanedimethanol, tricyclodecanedimethanol, neo-pentylglycol, 3-methyl-1,5-pentanediol, 1,6-hexanediol, 1,10-decanediol, polyethylene glycols with different molecular weights, polypropylene glycols with different molecular weights, pentaerythritol, dipentaerythritol, ditrimethylolpropane, diglycerol, triglycerol, polyglycerols with different molecular weights, and correspondingly ethoxylated and/or propoxylated derivatives.

Besides the OH groups, the polyols may optionally also contain further functional groups, more particularly those which are inert under the reaction conditions, examples being polyether polyols or polyurethane polyols.

Esterification catalysts used are strong organic or inorganic acids having a pKa of 2.5 or less. Typical examples of strong organic acids are, for instance, methanesulfonic acid and p-toluenesulfonic acid; examples of strong inorganic acids are, for instance, sulfuric acid and phosphoric acid. It is also possible, though, to use strongly acidic ion exchanger resins and zeolites.

As suitable polymerization inhibitors it is possible for example to use quinones, alkylphenols, alkoxyphenols and phenothiazines, with 4-methoxyphenol being particularly preferred. Further examples of suitable polymerization inhibitors can be found in WO-A-2009/106550.

As already stated, the reaction temperature is in the range from 70 to 150° C. It is preferred to operate in the range from 80 to 120° C.

As already stated, the water formed during the reaction is removed under reduced pressure, by which is meant a pressure of 600 hPa bar or less, from the reaction space. It is preferred to operate at pressures of 400 hPa bar or less.

A suitable vacuum gradient is set to remove the water of reaction, formed in the esterification, rapidly and effectively. The water of reaction in this case is distilled off as a water/(meth)acrylic acid mixture, with operation taking place preferably in reactors equipped with dephlegmators or distillation columns Depending on the separation performance and the reflux ratio, dephlegmators or distillation columns strip off a vapor phase enriched in the lower-boiling water, while the liquid reflux is enriched in the higher-boiling (meth)acrylic acid. In this way, the evaporation losses of (meth)acrylic acid that occur in each case are minimized, and the use of raw materials is optimized In one preferred embodiment, the polyols, the polymerization inhibitor and the acidic catalyst are charged to a reactor, through which air is passed, and then the first portion of (meth)acrylic acid is metered in, the total amount of (meth) acrylic acid added being set preferably at a level in the range of 105-160 mol %.

After reduction of the pressure and heating to the reaction temperature, a vacuum gradient (see FIG. 1) is applied, and so the reaction mixture is held continuously at boiling over a fixed time period, in order to remove the water of reaction as far as possible completely from the reaction mixture. Each subsequent portion of (meth)acrylic acid is added—and hence the next process stage initiated—preferably only when the acid number of the reaction mixture has dropped to a level of 100 mg KOH/g. In one or more embodiments, before the last process stage is initiated, the acid number ought to have dropped below a level of 50 mg KOH/g.

The procedure outlined for the first process stage is then repeated for the further process stages as well. In one of these subsequent operating stages, optionally, not only further acidic catalyst but also polymerization inhibitor can be added.

The reaction mixture can be worked up, for example, by neutralization, washing and filtration in accordance with all of the methods that are known in this context to the skilled person.

EXAMPLES

1. Substances Used

Acrylic acid—BASF SE (CAS number 79-10-7, molecular weight: 72.06 g/mol)

Tripropylene glycol—LyondellBasell (CAS number 24800-44-0, molecular weight: 192.26 g/mol)

Methanesulfonic acid (70% by weight)—BASF SE (CAS number 75-75-2, molecular weight: 96.10 g/mol)

Sulfuric acid (95% by weight)—Quaron France (CAS number 7664-93-9, molecular weight: 98.08 g/mol)

Phosphinic acid (50% by weight)—Minakem S.A.S. (CAS number 6303-21-5, molecular weight: 66.00 g/mol)

4-Methoxyphenol—Acros Chimica (CAS number 150-76-5, molecular weight: 124.14 g/mol)

Sodium carbonate, anhydrous—Quaron France (CAS number 497-19-8, molecular weight: 105.99 g/mol)

Sodium carbonate decahydrate—Disachim S.A. (CAS number 6132-02-1, molecular weight: 286.14 g/mol)

Sodium sulfate, anhydrous—Brenntag N.V. (CAS number 7757-82-6, molecular weight: 142.04 g/mol)

Dicalite 4158 (natural sodium/potassium/aluminum silicate)—Dicalite Europe N.V. (CAS number 93763-70-3)

2. Measurement and Test Methods

Acid number: standard NF EN ISO 660

Water content: standard ISO 4317
APHA color: standard ISO 6271
Viscosity: standard ISO 2555
Gas chromatography:
  Gas chromatograph: 430-GC from Varian
  Column: CP-Sil 8 CB (10 m length, 0.15 mm internal diameter, film thickness 0.12 μm) from Agilent Technologies
  Carrier gas: helium
  Injection volume: 5.0 μ
  Split injection: 1:100
  Detector: flame ionization
  Injector temperature: 300° C.
  Detector temperature: 350° C.
  Temperature program: 120° C. for 2 minutes, heating 120-300° C. at 20° C. per minute/300° C. for 5 minutes
  Sample preparation: none (direct injection)
  Peak assignment, gas chromatography:
Indicated below are the retention times of certain substances, together with their structure and the chemical identification:
Retention time=3.6 minutes

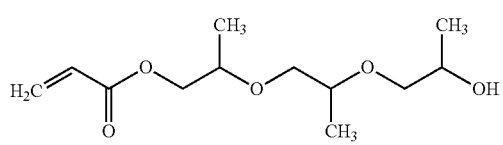 [SMILES: C=CC(=O)OCC(C)OCC(C)OCC(C)O]

Tripropylene Glycol Monoacrylate

Retention time=5.2 minutes

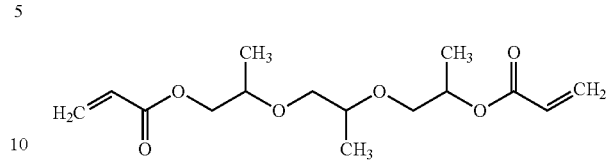

Tripropylene Glycol Diacrylate

Retention time=6.0 minutes

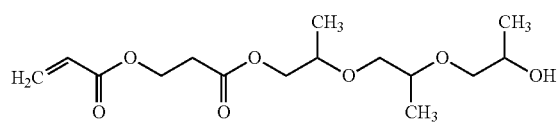 [SMILES: C=CC(=O)OCCC(=O)OCC(C)OCC(C)OCC(C)O]

Michael Adduct Tripropylene Glycol Monoacrylate/Acrylic Acid

Retention time=7.0 minutes

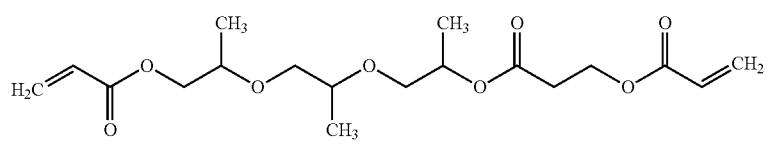 [SMILES: C=CC(=O)OCCC(=O)OC(C)COC(C)COC(C)COC(=O)C=C]

Michael Adduct Tripropylene Glycol Diacrylate/Acrylic Acid

Retention time=9.3 minutes

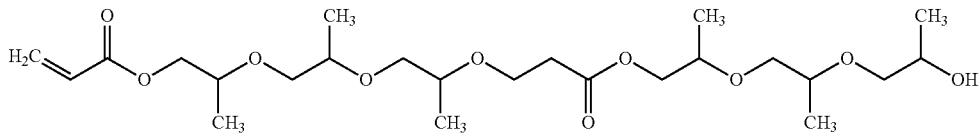 [SMILES: C=CC(=O)OCC(C)OCC(C)OCC(C)OCCC(=O)OCC(C)OCC(C)OCC(C)O]

Michael Adduct Tripropylene Glycol Monoacrylate/Tripropylene Glycol Monoacrylate Retention time=10.0 minutes

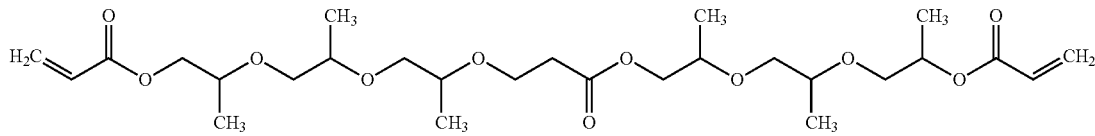 [SMILES: C=CC(=O)OCC(C)OCC(C)OCC(C)OCCC(=O)OCC(C)OCC(C)OCC(C)OC(=O)C=C]

Michael Adduct Tripropylene Glycol Diacrylate/Tripropylene Glycol Monoacrylate

3. Working Examples

Example 1

Inventive

A 25 m³ reactor was charged at a reactor temperature of 45° C. with 10 400 kg (54 093 mol) of tripropylene glycol, with a constant stream of air being passed through the reactor, and then a vacuum of 300 hPa was set.

In the first stage, in succession and with stirring, 15 kg (121 mol) of 4-methoxyphenol, 1197 kg (16 611 mol) of acrylic acid, 188 kg (1424 mol) of 50% strength by weight phosphinic acid and 188 kg (1821 mol) of 95% strength by weight sulfuric acid were added. The temperature of the reaction mixture was subsequently raised to 90° C. Under these temperature/pressure conditions, the direct esterification commenced, with a mixture of water of reaction and acrylic acid being removed continuously by distillation in line with the composition of the boiling curve of the respective phase equilibrium state. After 1 hour, the pressure was lowered in steps, with the reaction mixture at a constant temperature, initially to 150 hPa in 0.25 h and finally to 100 hPa in 0.75 h. The pressure of 100 hPa was maintained until the acid number of the reaction mixture had dropped below 40 mg KOH/kg. The pressure was subsequently raised again to 300 hPa.

In the second stage, 1197 kg (16 611 mol) of acrylic acid were added, the pressure was held at 300 hPa for 0.75 h, then lowered to 130 hPa over 0.15 h and finally run down to 70 hPa over 1 h. The pressure of 70 hPa was maintained until the acid number of the reaction mixture had dropped below 50 mg KOH/kg. The pressure was subsequently raised again to 300 hPa.

In the third stage, 1197 kg (16 611 mol) of acrylic acid were added, the pressure was held at 300 hPa for 0.85 h, then lowered to 200 hPa over 0.15 h and finally run down to 60 hPa over 1 h. The pressure of 60 hPa was maintained until the acid number of the reaction mixture had dropped below 60 mg KOH/kg. The pressure was subsequently raised again to 300 hPa.

In the fourth stage, 1197 kg (16 611 mol) of acrylic acid were added, the pressure was held at 300 hPa for 0.85 h, then lowered to 120 hPa over 0.15 h and finally run down to 60 hPa over 1 h. The pressure of 60 hPa was maintained until the acid number of the reaction mixture had dropped below 60 mg KOH/kg. The pressure was subsequently raised again to 300 hPa.

In the fifth stage, 1197 kg (16 611 mol) of acrylic acid were added, the pressure was held at 300 hPa for 0.85 h, then lowered to 120 hPa over 0.15 h and finally run down to 90 hPa over 1 h. The pressure of 90 hPa was maintained until the acid number of the reaction mixture had dropped below 70 mg KOH/kg. The pressure was subsequently raised again to 300 hPa.

In the sixth stage, 1197 kg (16 611 mol) of acrylic acid and also 126 kg (918 mol) 70% strength by weight methanesulfonic acid were added, the pressure was held at 300 hPa for 0.5 h, then lowered to 250 hPa over 0.35 h, to 140 hPa over 0.15 h and finally run down to 80 hPa over 1.5 h. The pressure of 80 hPa was maintained until the acid number of the reaction mixture had dropped below 80 mg KOH/kg. The pressure was subsequently raised again to 300 hPa.

In the seventh stage, 1197 kg (16 611 mol) of acrylic acid were added, the pressure was held at 300 hPa for 0.1 h, then lowered to 140 hPa over 0.4 h and finally run down to 80 hPa over 3 h. The pressure of 80 hPa was maintained until the acid number of the reaction mixture had dropped below 100 mg KOH/kg. The pressure was subsequently raised again to 300 hPa.

In the eighth and last stage, 1197 kg (16 611 mol) of acrylic acid were added, the pressure was held at 300 hPa for 0.1 h, lowered to 130 hPa over 0.9 h, lowered to 80 hPa over 1.7 h, lowered to 50 hPa over 0.7 h, held for 1.5 h and finally run down to 10 hPa over 1.2 h. The pressure of 10 hPa was maintained until the acid number of the reaction mixture had dropped below 30 mg KOH/kg. The pressure thereafter was set to atmospheric pressure.

FIG. 1 shows the pressure set over the reaction time, with
Addition 1: 15.35 mol % acrylic acid
Addition 2: 15.35 mol % acrylic acid
Addition 3: 15.35 mol % acrylic acid
Addition 4: 15.35 mol % acrylic acid
Addition 5: 15.35 mol % acrylic acid
Addition 6: 15.35 mol % acrylic acid
Addition 7: 15.35 mol % acrylic acid
Addition 8: 15.35 mol % acrylic acid
Reaction temperature: 90° C.

Figure 2:
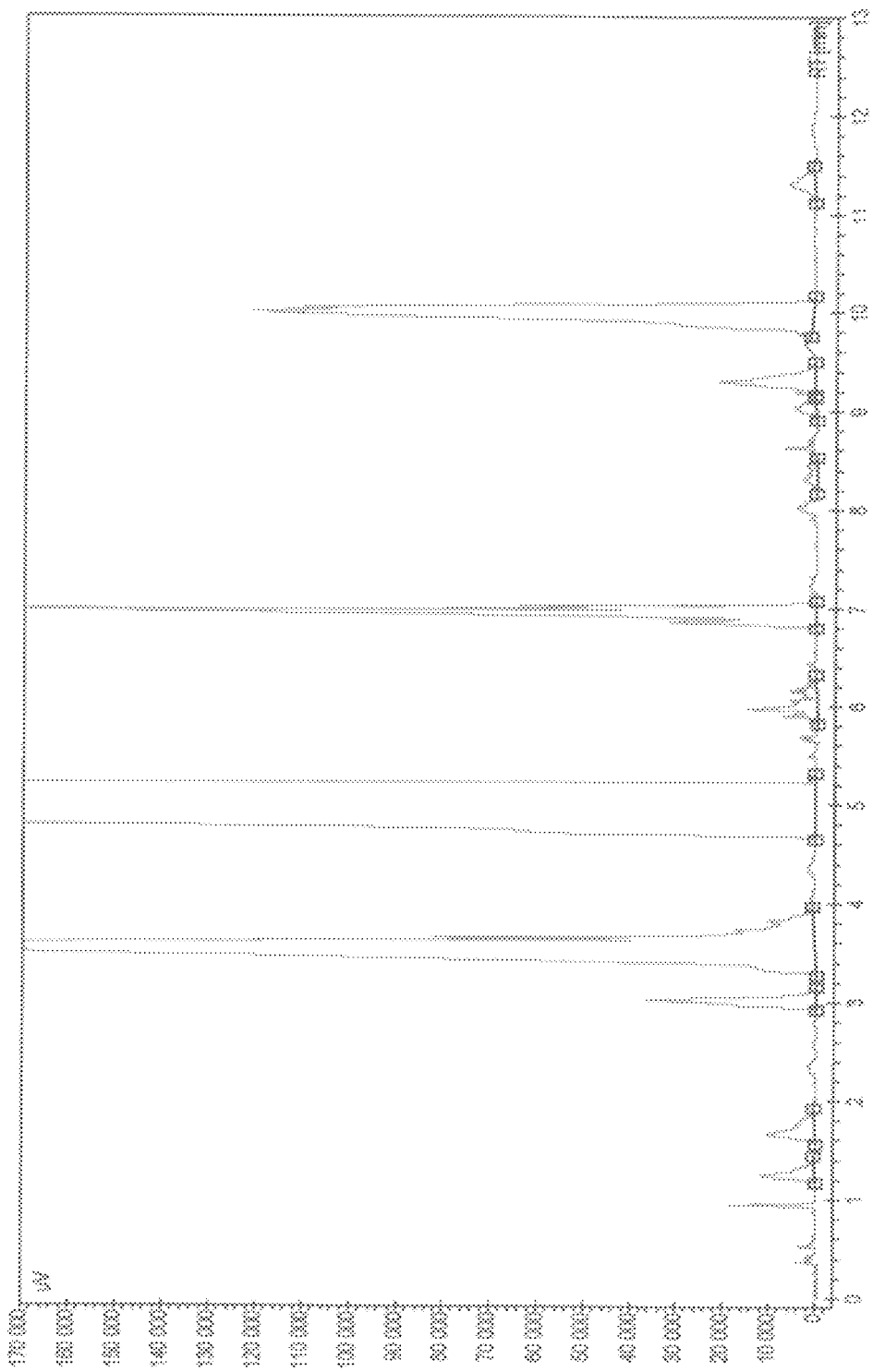
FIG. 2 shows a gas chromatographic analysis of a product in accordance with one or more embodiments of the present invention.

The 16 623 kg of crude product obtained in this way were cooled to 55° C. and then introduced with stirring into 3302 kg of a 15% strength by weight solution of anhydrous sodium carbonate in demineralized water, which was set likewise at 55° C. With stirring, 200 kg of sodium carbonate decahydrate were slowly added, and stirring was continued at 55° C. for 2 hours. The mixture was then left to stand at 55° C. for 3 hours, without stirring, and the aqueous phase was subsequently removed. The water content of the remaining 15 312 kg of crude product was found to be 2.3%. Thereafter the crude product was washed with stirring at 55° C., with introduction of 3652 kg of an 8.4% strength by weight solution of anhydrous sodium sulfate in demineralized water, and stirring was continued at this temperature for 0.75 hour. The mixture was then left to stand at 55° C. for 5 hours, without stirring, and the aqueous phase was subsequently removed. The crude product which remained was dried under vacuum with stirring, with air being passed through, at 55° C., the pressure in the first step being lowered from 1013 hPa to 170 hPa in 3.5 h, followed by 0.7 h at 90 hPa and finally by 0.9 h at 10 hPa. For the concluding purification and filtration, the crude product was cooled to 40° C. with stirring, admixed with the filtration aid Dicalite 4158 and then passed through a filter press. This gave 15 000 kg of end product with the following analytical data:
Acid number→0.15 mg KOH/g
Water content→0.15% by weight
APHA color→36
Viscosity (25.0° C.)→14 mPa·s GC analysis of the end product (FIG. 2) gave the following composition (GC area-percent):
Tripropylene glycol monoacrylate: 9.582%
Tripropylene glycol diacrylate: 80.873%
Michael adducts:
   Tripropylene glycol monoacrylate/acrylic acid: 0.379%
   Tripropylene glycol diacrylate/acrylic acid: 2.957%
   Tripropylene glycol monoacrylate/tripropylene glycol monoacrylate: 0.508%
   Tripropylene glycol diacrylate/tripropylene glycol monoacrylate: 4.160% Remainder: 1.541%

Comparative Example

A 25 m³ reactor was charged at a reactor temperature of 45° C. with 10 400 kg (54 093 mol) of tripropylene glycol, with a constant stream of air being passed through the reactor, and the pressure was lowered to 400 hPa. Then, in succession and with stirring, 15 kg (121 mol) of 4-methoxyphenol, 7768 kg (107 799 mol) of acrylic acid, 188 kg (1424 mol) of 50% strength by weight phosphinic acid and 188 kg (1821 mol) of 95% strength by weight sulfuric acid were added. The temperature of the reaction mixture was subsequently raised to 85° C. and the pressure was lowered to 370 hPa.

Under these temperature and pressure conditions, the direct esterification commenced, with a mixture of water of reaction and acrylic acid being removed continuously by distillation in line with the composition of the boiling curve of the respective phase equilibrium state. After 0.5 h, the pressure, with the reaction mixture at constant temperature, was reduced in steps, first to 250 hPa in 0.5 h, then to 215 hPa in 0.75 h and finally to 100 hPa in 5.5 h. The pressure of 100 hPa was maintained until the acid number of the reaction mixture had dropped below 140 mg KOH/kg. The pressure was subsequently raised to 370 hPa again and a further 904 kg (12 545 mol) of acrylic acid and 126 kg (918 mol) of 70% strength by weight methanesulfonic acid were added. The pressure, subsequently, was lowered in steps again to 155 hPa in 0.75 h and then to 90 hPa in 2 h, this pressure being maintained until the acid number of the reaction mixture had dropped below 120 mg KOH/g. The pressure was then raised again to 370 hPa and a further 904 kg (12 545 mol) of acrylic acid were added. To finish, the pressure was lowered again in steps to 120 hPa in 1.1 h, to 80 hPa in 1.7 h, then to 30 hPa in 4 h and finally to 5 hPa in 2.45 h. The pressure of 5 hPa was maintained until the acid number of the reaction mixture had reached 30 mg KOH/g. The pressure thereafter was set to atmospheric pressure.

Figure 3:
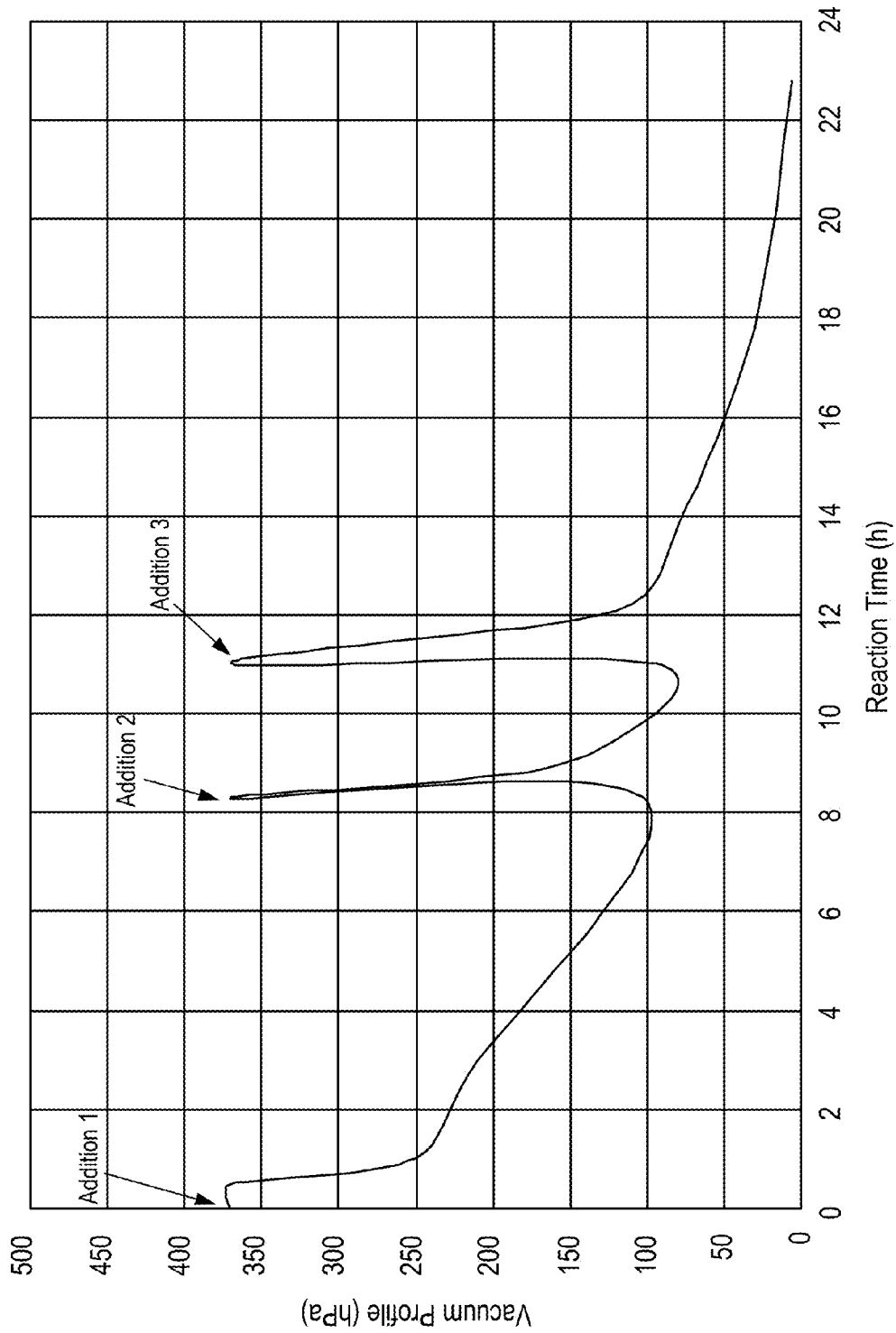
FIG. 3 is a graph showing the vacuum profile versus a reaction time during a process stage of a comparative reaction.

FIG. 3 shows the pressure set over the reaction time, with
Addition 1: 99.64 mol % acrylic acid
Addition 2: 11.60 mol % acrylic acid
Addition 3: 11.60 mol % acrylic acid
Reaction temperature: 85° C.

The 16 623 kg of crude product obtained in this way were cooled to 55° C. and then introduced with stirring into 3302 kg of a 15% strength by weight solution of anhydrous sodium carbonate in demineralized water, which was set likewise at 55° C., for neutralization. With stirring, 200 kg of sodium carbonate decahydrate were slowly added, and stirring was continued at 55° C. for 2 hours. The mixture was then left to stand at 55° C. for 3 hours, without stirring, and the aqueous phase was subsequently removed. The water content of the remaining 15 312 kg of crude product was determined, and thereafter the crude product was washed with stirring at 55° C., with introduction of 3652 kg of an 8.4% strength by weight solution of anhydrous sodium sulfate in demineralized water, and stirring was continued at this temperature for finally 0.75 hour. The mixture was then left to stand at 55° C. for 5 hours, without stirring, and the aqueous phase was subsequently removed.

Figure 4:
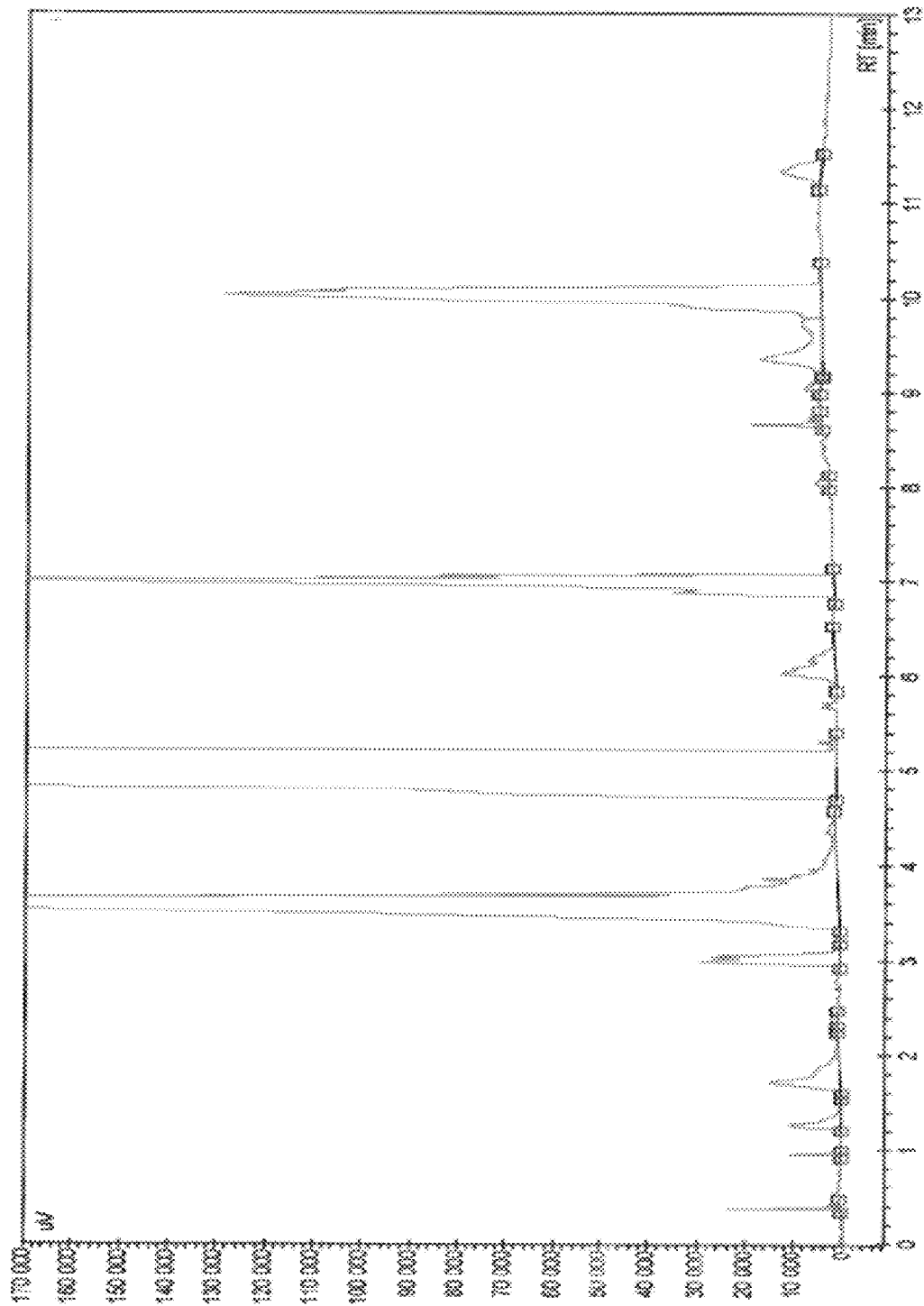
FIG. 4 shows a gas chromatographic analysis of a comparative product.

The crude product which remained was dried under vacuum with stirring, with air being passed through, at 55° C., the pressure in the first step being lowered from 1013 hPa to 170 hPa in 3.5 h, followed by 0.7 h at 90 hPa and finally by 0.9 h at 10 hPa. For filtration, the crude product was cooled to 40° C. with stirring, admixed with the filtration aid Dicalite 4158 and then placed in a filter press. This gave 15 000 kg of end product with the following analytical data:
Acid number→0.10 mg KOH/g
Water content→0.20% by weight
APHA color→8
Viscosity (25.0° C.)→13 mPa·s GC analysis of the end product (FIG. 4) gave the following composition (GC area-percent):
Tripropylene glycol monoacrylate: 12.021%
Tripropylene glycol diacrylate: 76.092%
Michael adducts:
  Tripropylene glycol monoacrylate/acrylic acid: 0.461%
  Tripropylene glycol diacrylate/acrylic acid: 4.348%
  Tripropylene glycol monoacrylate/tripropylene glycol monoacrylate: 0.637%
  Tripropylene glycol diacrylate/tripropylene glycol monoacrylate: 4.435%
Remainder: 2.006%

The invention is:

1. A process for preparing (meth)acrylic esters of polyols, in which for 80 mol % or more of the esters, all of the OH groups of the polyols are esterified, the method comprising:
    reacting polyols with (meth)acrylic acid in the presence of acidic esterification catalysts and in the presence of polymerization inhibitors in a reaction space comprising a gas phase to produce a resultant water of condensation, wherein the reaction is operated with reaction mixtures which are liquid at reaction temperature and are free from nonreacting solvents and/or azeotropic entrainers,
    stripping the resultant water of condensation from the gas phase of the reaction space, wherein (meth)acrylic acid is metered in three or more portions, with the following provisos:
    the amount of the individual (meth)acrylic acid portions is set in each case in the range
    from 5 to 40 mol %, based on the entirety of the OH groups of the polyols used,
    the number of (meth)acrylic acid portions, multiplied by the amount of (meth)acrylic acid
    portions used (in mol %), produces a figure of at least 100 (mol %),
    the reaction is carried out at a temperature in the range from about 70 to about 150° C., and
    water formed in the reaction is removed from the reaction space under a reduced pressure.

2. The process according to claim 1, further comprising applying a vacuum gradient after adding each (meth)acrylic acid portion during the reaction, such that the reaction mixture boils continuously.

3. The process according to claim 1, wherein the water formed in the reaction is removed from the reaction space continuously.

4. The process according to claim 1, wherein one or more subsequent (meth)acrylic acid portions are added when the acid number of the reaction mixture has dropped below a level of 100 mg KOH/g.

5. The process according to claim 4, wherein the acid number of the reaction mixture after adding one of the three or more portions of (meth)acrylic acid is equal to or higher than the acid number prior to adding the one portion of (meth) acrylic acid, with the proviso that the acid number after the last portion of (meth)acrylic acid is added is lower than the acid number after the portion of (meth)acrylic acid preceding the last portion of (meth)acrylic acid is added.

6. The process according to claim 1, wherein the (meth) acrylic acid is metered in 4 to 16 portions.

7. The process according to claim 6, wherein the (meth) acrylic acid is metered in an equal amount in each portion.

8. The process according to claim 1, wherein the amount of each (meth)acrylic acid portion is in the range from 10 to 20 mol %.

9. The process according to claim 1, wherein the total amount of the (meth)acrylic acid portions metered in is 105 to 160 mol %, based on the entirety of the OH groups of the polyols used.

10. The process of claim 1, wherein the water removed from the reaction space is removed at a pressure of about 600 hPa or less.

* * * * *